United States Patent [19]

Firth et al.

[11] 4,198,850
[45] Apr. 22, 1980

[54] GAS SENSORS

[75] Inventors: Jack G. Firth, St. Albans; Alan Jones; Thomas A. Jones, both of Sheffield; Brenda Mann, Barnsley, all of England

[73] Assignee: National Research Development Corporation, London, England

[21] Appl. No.: 911,219

[22] Filed: May 31, 1978

[30] Foreign Application Priority Data

Nov. 30, 1977 [GB] United Kingdom ............ 49879/77

[51] Int. Cl.² ............................................. G01N 31/00
[52] U.S. Cl. ........................................................ 73/23
[58] Field of Search ............. 73/23; 338/34; 340/634; 23/232 E, 254 E; 324/71 SN; 357/10, 25

[56] References Cited

U.S. PATENT DOCUMENTS

| 3,695,848 | 10/1972 | Taguchi | 73/27 R |
| 3,999,947 | 12/1976 | Mihara et al. | 73/23 |
| 4,081,764 | 3/1978 | Christmann et al. | 357/10 |

FOREIGN PATENT DOCUMENTS 678337 9/1952 United Kingdom.
688860 3/1953 United Kingdom.

Primary Examiner—Anthony V. Ciarlante
Attorney, Agent, or Firm—Cushman, Darby & Cushman

[57] ABSTRACT

In a gas-sensitive resistor of the metal oxide type, the sensitive body is a single crystal of zinc oxide. Such a sensor has particular application in the testing of oxygen-containing atmospheres for the presence of carbon monoxide.

5 Claims, 4 Drawing Figures

GAS SENSORS

This invention relates to gas sensors of the kind comprising a body of a semiconducting metal oxide exposed for contact with an atmosphere to be tested, and a pair of electrodes separately in contact with said body.

Such sensors operate by virtue of the changes of electrical conductivity which can be induced in semiconducting metal oxides by the adsorption or reaction of gases on their surfaces; thus in use of such a sensor changes in the concentration of a gas to be sensed in an atmosphere to which the sensor is exposed are detected by monitoring the resistance of the resistor constituted by the oxide body and the electrodes. Important characteristics in respect of the performance of a particular gas sensor of the kind specified are its sensitivity of the gas to be sensed, which may conveniently be specified in terms of the proportional change in resistance for a given change in concentration of the gas to be sensed, its selectivity in terms of the responses to different gases which may be present in the atmosphere to be tested, and its speed of response to changes in the concentration of the gas to be sensed. It is, of course, desirable that the sensor should exhibit a high degree of stability with time, both in respect of these characteristics and in respect of the value of the resistance measured for a given concentration of the gas to be sensed. For a given oxide, the sensitivity and selectivity for a given application commonly vary markedly with temperature, so that it is normally desirable to maintain the oxide body of a gas sensor of the kind specified within an appropriate temperature range to achieve an optimum combination of operating characteristics; it is usual for this purpose to provide the sensor with an associated electric resistance heater. The sensitivity and selectivity can also be influenced by the incorporation of appropriate metallic impurities into the semiconducting oxide lattice, as disclosed in British Patent Specification No. 1,374,575.

In known gas sensors of the kind specified, it has been usual to employ a porous oxide body, such as may be produced either by compacting a powder of the oxide or by depositing from solution a mass of small crystallites of the oxide; it is also known to employ an oxide body in the form of a thin film deposited on a suitable substrate by a technique such as vacuum deposition. Such forms of oxide body have apparently been utilised because they exhibit a relatively high ratio of surface area to volume, it having been assumed that this was necessary in order to achieve a relatively high value for the sensitivity. The use of such forms of oxide body has, however, been found to entail a tendency to instability in the characteristics of the gas sensors, which in some cases is so severe as to render impracticable the choice for a particular application of a specific oxide which would otherwise be suitable in respect of sensitivity and selectivity. One such case concerns the testing of oxygen-containing atmospheres for the presence of carbon monoxide; attempts to utilise for this purpose known forms of gas sensor of the kind specified employing zinc oxide (ZnO) have given unsatisfactory results because of instability of the sensor characteristics, although the choice of this oxide would otherwise be suitable for the purpose in question.

According to one aspect of the present invention there is provided a gas sensor of the kind specified in which the oxide body is a single crystal of zinc oxide.

According to another aspect of the invention there is provided a method of testing an oxygen-containing atmosphere for the presence of carbon monoxide, comprising monitoring the electrical resistance of a single crystal of zinc oxide while the crystal is exposed to said atmosphere and is maintained at a substantially constant temperature in the range 300°–420° C.

The invention is in part based on the surprising discovery that, for the purpose of testing oxygen-containing atmospheres for the presence of carbon monoxide, it is possible when using a single crystal of zinc oxide in the gas sensor of the kind specified to obtain values of sensitivity which are not greatly inferior to those obtainable with the known sensors when using zinc oxide, notwithstanding the relatively low ratio of surface area to volume necessarily exhibited by a single crystal. With this is coupled the fact that the relevant properties of single crystals of zinc oxide are much more stable with time than those of bodies of zinc oxide of the forms used in the known sensors.

The invention will be further described with reference to the accompanying drawings, in which.

Figure 1:
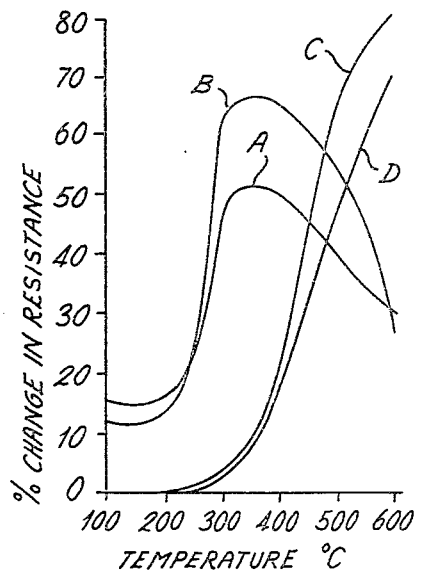
FIGS. 1 and 2 are explanatory diagrams.

The factors underlying the invention may conveniently be exemplified by consideration of a specific potential application for gas sensors of the kind specified, namely the detection and measurement in air of carbon monoxide in a concentration range of 0–100 parts per million, in the presence of methane at a concentration of the order of 1% and water vapour at any relative humidity in the range 0–100%. Initial experiments indicated that for this application zinc oxide without any deliberately added impurity could exhibit an appropriate combination of sensitivity and selectivity for employment in a gas sensor of the kind specified. FIG. 1 illustrates for example results obtained when using this oxide in a gas sensor having a form similar to that shown in FIG. 1 of British Patent Specification No. 1,374,575; the oxide in this case was in the form of a mass of small crystallites deposited from a molten ammonium nitrate solvent on the surface of a glass bead, the electrodes being platinum wires partly embedded in the bead and the sensor being provided with an electric resistance heater in the form of a coil of wire embedded in the bead. The results illustrated in FIG. 1 were obtained with a freshly fabricated sensor by measuring the D.C. resistance of the oxide between the electrodes over a range of temperatures in the following atmospheres:

(1) dry air;
(2) dry air containing 100 p.p.m. carbon monoxide;
(3) air saturated with water vapour and containing 100 p.p.m. carbon monoxide;
(4) dry air containing 1% methane;
(5) air saturated with water vapour and containing 1% methane.

Curves A, B, C and D in FIG. 1 show the resultant variations with temperature of the percentage change in resistance as between case (1) and cases (2), (3), (4) and (5) respectively. As will be seen, the sensor exhibited a significant sensitivity to carbon monoxide over a range of temperatures, coupled with a reasonable degree of selectivity against methane and water vapour at the lower end of this range. Further tests in respect of stability have, however, shown that such a sensor would in practice be unsuitable for the application envisaged, since at an appropriate operating temperature both the sensitivity to carbon monoxide and the basic resistance in dry air vary to an unacceptable extent within a period of hours.

Figure 2:
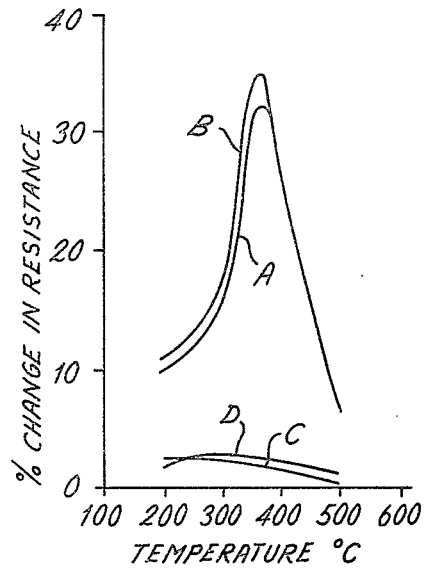

FIG. 2 illustrates comparable results obtained with a single crystal of zinc oxide. In this case the crystal was heated to the required temperature by mounting it in a furnace, and two electrodes were provided in the form of gold members which were simply pressed into contact with the crystal. Measurements of the D.C. resistance of the crystal between the electrodes were made in the same atmospheres as referred to above, the annotations of the curves A, B, C and D in FIG. 2 having the same significance as for FIG. 1. It will be seen that as compared with the previous case the peak value of the sensitivity to carbon monoxide is somewhat reduced, but is still of the same order of magnitude, while a high degree of selectivity against methane and water vapour is displayed at the temperature corresponding to the peak value of sensitivity to carbon monoxide. Further tests on single crystals of zinc oxide in respect of stability have shown that the significant characteristics do not vary with time to an unacceptable degree. For instance, in one experiment involving continuous operation for a period of twenty days at a temperature of 370° C. (corresponding to the peak of the sensitivity to carbon monoxide), the variations of the response to 100 p.p.m. carbon monoxide lay within a range of ±8% of the mean value, the variations of the response to 1% methane lay within a range of ±20% of the mean value, and the variations of the resistance measured in dry air lay within a range of ±10% of the mean value; no measurable variations were detected in the speed of response to changes in carbon monoxide concentration.

As indicated, the results for single crystals discussed above were obtained with gold electrodes pressed into contact with the oxide. Such contacts may be found to exhibit non-ohmic characteristics, but this fact does not appear to have any particular significance in the present context, since similar results have been obtained with electrodes in the form of vacuum deposited layers of gold, where the contact is of an ohmic nature. It should be noted, however, that results which are less satisfactory in respect of stability have been encountered when using zinc oxide single crystals with electrodes of platinum-ruthenium alloy pressed into contact with the oxide. The reason for this is not clear, but it is believed that it may be due to catalytic activity of the electrode material. It is therefore thought preferable, at least in the case of the specific application mentioned, to use gold (or possibly silver) as the electrode material in a gas sensor according to the invention, and to avoid the use for this purpose of metals of Group VIII of the Periodic Table.

Figure 3:
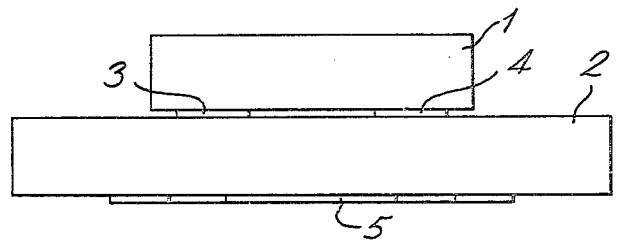
FIGS. 3 and 4 are respectively a side elevation and a plan of a gas sensor according to the invention.
Figure 4:
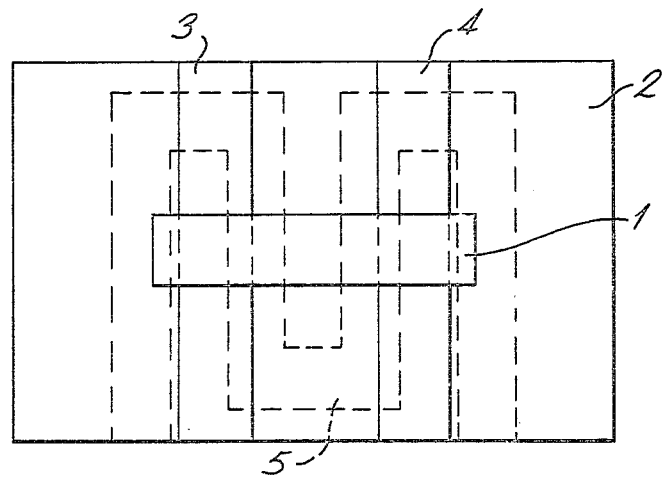

A practical embodiment of the invention is illustrated in FIGS. 3 and 4, which are respectively a side elevation and plan of a gas sensor intended for use in the specific application referred to above. The sensor comprises a single crystal 1 of zinc oxide in the form of a rod which may suitably have a length of about two mm. and a cross section about 0.5 mm. square. Such a crystal can for example be cut from a large monocrystalline body grown by one of the well known vapour-phase or liquid-phase techniques; an alternative possibility would be to utilise a needle-like crystal such as may be grown by the method described by Kashyap in Journal of Applied Physics, Volume 44, pages 4381-4. The crystal 1 is mounted on a substrate 2 consisting of a wafer of an alumina ceramic, suitably about 0.5 mm. thick, the substrate 2 having on one main face two parallel strips 3 and 4 of gold which are formed by vacuum deposition and which constitute the electrodes of the sensor; the strips 3 and 4 may suitably have a thickness of the order of one micron. The mounting of the crystal 1 is effected by holding it in contact with the strips 3 and 4 and heating the structure to about 500° C. On the opposite main face of the substrate 2 is provided an electric resistance heater 5 in the form of a convoluted strip of platinum, which may for example be deposited by a technique such as is used in the fabrication of printed circuits. It should be noted that in FIG. 3 the thicknesses of the strips 3, 4 and 5 have been greatly exaggerated for the sake of clarity. Leads (not shown) for the sensor may suitably be provided in the form of gold or platinum wires welded to the electrodes 3 and 4 and the ends of the heater 5.

In use the sensor is exposed to an atmosphere to be tested for the presence of carbon monoxide, and is connected in a detection system having provision for energising the heater 5 so as to maintain the crystal 1 at a substantially constant temperature within the range 300°–420° C., and also having provision for measuring the resistance of the crystal 1 between the electrodes 3 and 4. A suitable type of system for this purpose is disclosed in British Patent Specification No. 1,451,231. It may be noted here that, at an operating temperature in the range indicated, the resistance in normal air for a sensor as just described will typically have a value of the order of a few kilohms.

In the case of the specific application discussed above, it is unnecessary for any impurity to be added deliberately to the zinc oxide single crystal. In other cases, however, it may be desired to influence the sensitivity and/or selectivity for a given application by the incorporation of a metallic impurity in the oxide lattice; in such cases the impurity may be introduced either during the growth of the single crystal or subsequently by diffusion into the crystal from an external source.

We claim:

1. A method of testing an oxygen-containing atmosphere for the presence of carbon monoxide, the method comprising:

exposing to said atmosphere a monocrystalline body of zinc oxide having a pair of electrodes separately in contact therewith, while maintaining said body at a substantially constant temperature in the range 300°–420° C.; and monitoring the electrical resistance of said body between said electrodes while said body is so exposed and maintained.

2. A gas sensor comprising:

a monocrystalline body of zinc oxide exposed of contact with an atmosphere to be tested;

a pair of electrodes separately in contact with said body; and a heater element juxtaposed with said body and operable to heat said body to a temperature of at least 300° C.

3. A gas sensor according to claim 2 wherein both of said electrodes are of a metal selected from the group consisting of gold and silver.

4. A gas sensor comprising:

a monocrystalline body of zinc oxide exposed for contact with an atmosphere to be tested;

a pair of electrodes separately in contact with said body;

an electrically insulating substrate supporting said body; and an electric resistance heater formed on said substrate.

5. A gas sensor according to claim 4 wherein both of said electrodes are of a metal selected from the group consisting of gold and silver.

* * * * *